(12) United States Patent
Greim et al.

(10) Patent No.: US 11,246,998 B2
(45) Date of Patent: Feb. 15, 2022

(54) AEROSOL-GENERATING SYSTEM WITH DIFFERENTIAL HEATING

(71) Applicant: Philip Morris Products S.A., Neuchatel (CH)

(72) Inventors: Olivier Greim, Yverdon-les-Bains (CH); Julien Plojoux, Geneva (CH); Ihar Zinovik, Peseux (CH); Evan Jochnowitz, Neuchatel (CH)

(73) Assignee: Philip Morris Products S.A., Neuchatel (CH)

(*) Notice: Subject to any disclaimer, the term of this patent is extended or adjusted under 35 U.S.C. 154(b) by 1006 days.

(21) Appl. No.: 14/775,802

(22) PCT Filed: Mar. 14, 2014

(86) PCT No.: PCT/EP2014/055177
§ 371 (c)(1),
(2) Date: Sep. 14, 2015

(87) PCT Pub. No.: WO2014/140320
PCT Pub. Date: Sep. 18, 2014

(65) Prior Publication Data
US 2016/0022930 A1    Jan. 28, 2016

(30) Foreign Application Priority Data
Mar. 15, 2013  (EP) .................................... 13159398

(51) Int. Cl.
*A24F 40/30* (2020.01)
*A61M 11/04* (2006.01)
(Continued)

(52) U.S. Cl.
CPC ........... *A61M 11/042* (2014.02); *A24F 40/30* (2020.01); *A24F 40/42* (2020.01); *A24F 40/51* (2020.01);
(Continued)

(58) Field of Classification Search
CPC ........ A24F 47/008; A24F 40/00; A24F 40/10; A24F 40/30; A24F 40/42; A24F 40/46;
(Continued)

(56) References Cited

U.S. PATENT DOCUMENTS 5,093,894 A    3/1992 Deevi et al.
5,249,586 A *  10/1993 Morgan ................ A24F 47/008
                                                    128/200.14
(Continued)

FOREIGN PATENT DOCUMENTS

CN      1708241 A     12/2005
CN    101822420 A      9/2010
(Continued)

OTHER PUBLICATIONS

International Search Report dated Jun. 13, 2014 in PCT/EP2014/055177 Filed Mar. 14, 2014.
(Continued)

*Primary Examiner* — Michael H. Wilson
*Assistant Examiner* — Yana B Krinker
(74) *Attorney, Agent, or Firm* — Oblon, McClelland, Maier & Neustadt, L.L.P.

(57) ABSTRACT

An aerosol-generating system is provided, including an aerosol-generating article and an aerosol-generating device. The aerosol-generating article includes a first compartment having a first one of a volatile delivery enhancing compound source and a medicament source; and a second compartment having a second one of the volatile delivery enhancing compound source and the medicament source. The aerosol-generating device includes a cavity configured to receive the first compartment and the second compartment; and an external heater positioned about a perimeter of the cavity. The aerosol-generating device is configured to heat the first compartment and the second compartment so that the first (Continued)

compartment has a lower temperature than the second compartment.

19 Claims, 2 Drawing Sheets

(51) Int. Cl.
    *A61M 15/00*  (2006.01)
    *A61M 15/06*  (2006.01)
    *A24F 40/42*  (2020.01)
    *A24F 40/51*  (2020.01)
    *A24F 40/57*  (2020.01)
    *A24F 40/60*  (2020.01)
    *A24F 40/46*  (2020.01)
    *A24F 40/10*  (2020.01)

(52) U.S. Cl.
    CPC ......... *A24F 40/57* (2020.01); *A61M 15/0003* (2014.02); *A61M 15/0035* (2014.02); *A61M 15/06* (2013.01); *A24F 40/10* (2020.01); *A24F 40/46* (2020.01); *A24F 40/60* (2020.01); *A61M 11/047* (2014.02); *A61M 2205/3368* (2013.01); *A61M 2205/364* (2013.01); *A61M 2205/3653* (2013.01); *A61M 2205/8206* (2013.01)

(58) Field of Classification Search
    CPC ........ A24F 40/57; A24F 47/00; A24F 47/002; A24F 47/004; A24F 40/40; A24F 40/51; A24F 40/60; A61M 15/06; A61M 15/0003; A61M 11/042; A61M 11/047; A61M 2205/364; A61M 2205/3653; A61M 2205/8206; A61M 2205/3368; A51M 15/0035; A51M 15/06; A51M 15/0003
    See application file for complete search history.

(56) References Cited

U.S. PATENT DOCUMENTS

| | | | |
|---|---|---|---|
| 6,234,167 B1 * | 5/2001 | Cox | A61M 15/0003 128/200.14 |
| 8,322,350 B2 | 12/2012 | Lipowicz | |
| 2004/0129280 A1 | 7/2004 | Woodson et al. | |
| 2005/0045193 A1 | 3/2005 | Yang | |
| 2006/0283468 A1 | 12/2006 | Lipowicz | |
| 2007/0256697 A1 | 11/2007 | Yang | |
| 2009/0293888 A1 * | 12/2009 | Williams | A24F 47/008 131/178 |
| 2011/0126848 A1 * | 6/2011 | Zuber | A24F 47/008 131/329 |
| 2011/0155153 A1 | 6/2011 | Thorens et al. | |
| 2012/0048266 A1 | 3/2012 | Alelov | |
| 2012/0204889 A1 | 8/2012 | Xiu | |
| 2012/0227752 A1 | 9/2012 | Alelov | |
| 2013/0014755 A1 * | 1/2013 | Kumar | A24F 47/006 128/202.21 |
| 2013/0074854 A1 | 3/2013 | Lipowicz | |

FOREIGN PATENT DOCUMENTS

| | | | |
|---|---|---|---|
| EP | 0 438 862 | | 7/1991 |
| EP | 2 022 349 A1 | | 2/2009 |
| EP | 2 468 117 A1 | | 6/2012 |
| EP | 2 481 308 | | 8/2012 |
| JP | 2002-527153 A | | 8/2002 |
| JP | 2010-532672 | * 10/2010 | ............ A61M 13/00 |
| JP | 2010-532672 A | | 10/2010 |
| KR | 10-2012-0104183 A | | 9/2012 |
| RU | 103 281 U1 | | 4/2011 |
| UA | 78 167 U | | 3/2013 |
| WO | 2004 041007 | | 5/2004 |
| WO | 2006 070288 | | 7/2006 |
| WO | WO 2008/121610 A1 | | 10/2008 |
| WO | WO 2010/107613 A1 | | 9/2010 |
| WO | WO 2010/145805 A1 | | 12/2010 |
| WO | WO 2011/034723 A1 | | 3/2011 |
| WO | WO 2011/063970 A1 | | 6/2011 |
| WO | WO 2012/085203 A1 | | 6/2012 |
| WO | 2013/034459 A1 | | 3/2013 |
| WO | 2013 034460 | | 3/2013 |
| WO | WO 2013/060743 A2 | | 5/2013 |

OTHER PUBLICATIONS

Written Opinion dated Jun. 13, 2014 in PCT/EP2014/055177.
Office Action dated Dec. 18, 2017 in corresponding Japanese Patent Application No. 2015-562219 (with English Translation), 10 pages.
Combined Office Action and Search Report dated May 18, 2017 in Chinese Patent Application No. 201480009067.X (with English translation).
Office Action dated Mar. 6, 2018 in corresponding Russian Patent Application No. 2015144036 (with English Translation), 14 pages.
Office Action dated Nov. 17, 2016 in Kazakhstan Patent Application No. 2015/1098.1 (with English language translation).
Indian Office Action with English translation dated Aug. 19, 2019 in corresponding Indian Patent Application No. 4874/DELNP/2015, (6 pages).
Korean Office Action dated Aug. 19, 2020 in Patent Application No. 10-2015-7023047 (with English translation), 11 pages.

* cited by examiner

AEROSOL-GENERATING SYSTEM WITH DIFFERENTIAL HEATING

CROSS REFERENCE TO RELATED APPLICATION

This application is a U.S. national phase application under 35 U.S.C. § 371 of PCT/EP2014/055177, filed on Mar. 14, 2014, and claims the benefit of priority under 35 U.S.C. § 119 from prior EP Application No. 13159398.0, filed on Mar. 15, 2013, the entire contents of each of which are incorporated herein by reference.

The present invention relates to an aerosol-generating system and an aerosol-generating device for use in an aerosol-generating system. In particular, the present invention relates to an aerosol-generating system for generating an aerosol comprising nicotine salt particles and an aerosol-generating device for use in such an aerosol-generating system.

WO 2008/121610 A1, WO 2010/107613 A1 and WO 2011/034723 A1 disclose devices for delivering nicotine or other medicaments to a user comprising a volatile acid, such as pyruvic acid, or other volatile delivery enhancing compound source and a nicotine or other medicament source. The volatile delivery enhancing compound is reacted with nicotine in the gas phase to form an aerosol of nicotine salt particles that is inhaled by the user.

At room temperature pyruvic acid and nicotine are both sufficiently volatile to form respective vapours that react with one another in the gas phase to form nicotine pyruvate salt particles. However, the vapour pressure of pyruvic acid at room temperature is substantially greater than that of nicotine leading to a difference in the vapour concentration of the two reactants. Differences between the vapour concentration of the volatile delivery enhancing compound and nicotine in devices of the type disclosed in WO 2008/121610 A1, WO 2010/107613 A1 and WO 2011/034723 A1 can disadvantageously lead to the delivery of unreacted delivery enhancing compound vapour to a user.

It is desirable to produce a maximum quantity of nicotine salt particles for delivery to a user using a minimum quantity of reactants. Consequently, it would be desirable to provide an aerosol-generating system of the type disclosed in WO 2008/121610 A1, WO 2010/107613 A1 and WO 2011/034723 A1 in which the quantity of unreacted volatile delivery enhancing agent is minimised.

It would be especially desirable to provide an aerosol-generating system of the type disclosed in WO 2008/121610 A1, WO 2010/107613 A1 and WO 2011/034723 A1 in which the consistency of nicotine salt particle delivery to a user is improved.

According to the invention there is provided an aerosol-generating system comprising: an aerosol-generating article; and an aerosol-generating device. The aerosol-generating article comprises: a first compartment comprising a first one of a volatile delivery enhancing compound source and a medicament source; and a second compartment comprising a second one of the volatile delivery enhancing compound source and the medicament source. The aerosol-generating device comprises a cavity configured to receive the first compartment and the second compartment of the aerosol-generating article; and an external heater positioned about a perimeter of the cavity. The aerosol-generating device is configured to heat the first compartment and the second compartment of the aerosol-generating article so that first compartment of the aerosol-generating article has a lower temperature than the second compartment of the aerosol-generating article.

According to the invention there is also provided an aerosol-generating device for use in an aerosol-generating system according to the invention, the aerosol-generating device comprising: a cavity configured to receive an aerosol-generating article; an external heater comprising: a first external heating element configured to heat a first compartment of an aerosol-generating article received with the cavity; and a second external heating element configured to heat a second compartment of an aerosol-generating article received with the cavity; and a controller configured to control a supply of power to the first external heating element and the second external heating element so that the first external heating element has a lower temperature than the second external heating element.

According to the invention there is further provided an aerosol-generating device for use in an aerosol-generating system according to the invention, the aerosol-generating device comprising: a cavity configured to receive an aerosol-generating article; an external heater comprising: one or more heating elements; a first heat transfer element positioned between the one or more heating elements and the cavity; and a second heat transfer element positioned between the one or more heating elements and the cavity, wherein the first heat transfer element has a lower thermal conductivity than the second heat transfer element.

According to the invention there is additionally provided a method of controlling the formation of an aerosol of nicotine salt particles, the method comprising the steps of: controlling the release of a volatile delivery enhancing compound from a volatile delivery enhancing source in a first compartment of an aerosol-generating article by heating the first compartment; controlling the release of nicotine from a nicotine source in a second compartment by heating the second compartment; and allowing volatile delivery enhancing compound released from the volatile delivery enhancing source in the first compartment to react with nicotine released from the nicotine source in the second compartment in the gas phase to form an aerosol of nicotine salt particles, characterised in that the method comprises heating the first compartment to a temperature lower than the second compartment.

According to the invention there is yet further provided an aerosol-generating system comprising: an aerosol-generating article; and an aerosol-generating device. The aerosol-generating article comprises: a first compartment comprising a first one of a volatile delivery enhancing compound source and a medicament source; and second compartment comprising a second one of the volatile delivery enhancing compound source and the medicament source. The aerosol-generating device comprises a cavity configured to receive the first compartment and the second compartment of the aerosol-generating article; and an external heater positioned about a perimeter of the cavity. The aerosol-generating device is configured to heat the first compartment and the second compartment of the aerosol-generating article. The first compartment of the aerosol-generating article has a lower thermal conductivity than the second compartment of the aerosol-generating article.

As used herein, the term "aerosol-generating device" refers to a device that interacts with an aerosol-generating article to generate an aerosol that is directly inhalable into a user's lungs thorough the user's mouth.

As used herein, the term "aerosol-generating article" refers to an article comprising an aerosol-forming substrate capable of releasing volatile compounds, which can form an aerosol. In certain embodiments, the aerosol-generating article may comprise an aerosol-forming substrate capable of releasing upon heating volatile compounds, which can form an aerosol.

As used herein, the terms "external heater" and "external heating element" refer to a heater and heater element, respectively, that are positioned externally to an aerosol-generating article received in the cavity of the aerosol-generating device.

Differential heating of the delivery enhancing compound source and the medicament source of the aerosol-generating article by the aerosol-generating device of the aerosol-generating system of the invention allows precise control of the amount of volatile delivery enhancing compound vapour and medicament vapour released from the volatile delivery enhancing compound source and the medicament source respectively. This advantageously enables the vapour concentrations of the volatile delivery enhancing compound and the medicament to be controlled and balanced proportionally to yield an efficient reaction stoichiometry. This advantageously improves the efficiency of the formation of an aerosol and the consistency of the medicament delivery to a user. It also advantageously reduces the delivery of unreacted delivery enhancing compound vapour and unreacted medicament vapour to a user.

The first compartment comprises the one of the volatile delivery enhancing compound and the medicament having the higher vapour pressure. The second compartment comprises the one of the volatile delivery enhancing compound and the medicament having the lower vapour pressure.

In certain preferred embodiments the volatile delivery enhancing compound has a higher vapour pressure than the medicament. In such embodiments, the first compartment comprises the volatile delivery enhancing compound source and the second compartment comprises the medicament source.

In other embodiments the volatile delivery enhancing compound has a lower vapour pressure than the medicament. In such embodiments, the first compartment comprises the medicament source and the second compartment comprises the volatile delivery enhancing compound source.

The first compartment and the second compartment of the aerosol-generating article may abut one another. Alternatively, the first compartment and the second compartment of the aerosol-generating article may be spaced apart from one another. In certain preferred embodiments, the first compartment and the second compartment are spaced apart from one another in order to reduce heat transfer between the first compartment and the second compartment.

The first compartment of the aerosol-generating article may be sealed by one or more frangible barriers. In a preferred embodiment, the first compartment is sealed by a pair of opposed transverse frangible barriers.

Alternatively or in addition, the second compartment of the aerosol-generating article may be sealed by one or more frangible barriers. In a preferred embodiment, the second compartment is sealed by a pair of opposed transverse frangible barriers.

The one or more frangible barriers may be formed from any suitable material. For example, the one or more frangible barriers may be formed from a metal foil or film.

In such embodiments, the aerosol-generating device preferably further comprises a piercing member positioned within the cavity of the aerosol-generating device for piercing the one or more frangible barriers sealing one or both of the first compartment and the second compartment of the aerosol-generating article.

The volume of the first compartment and the second compartment may be the same or different. In a preferred embodiment, the volume of the second compartment is greater than the volume of the first compartment.

As described further below, the first compartment and the second compartment may be arranged in series or parallel within the aerosol-generating article.

As used herein, by "series" it is meant that the first compartment and the second compartment are arranged within the aerosol-generating article so that in use an air stream drawn through the aerosol-generating article passes through one of the first compartment and the second compartment and then passes through the other of the first compartment and the second compartment.

In embodiments in which the first compartment comprises the volatile delivery enhancing compound source and the second compartment comprises the medicament source, volatile delivery enhancing compound vapour is released from the volatile delivery enhancing compound source in the first compartment into the air stream drawn through the aerosol-generating article and medicament vapour is released from the medicament source in the second compartment into the air stream drawn through the aerosol-generating article. The volatile delivery enhancing compound vapour reacts with the medicament vapour in the gas phase to form an aerosol, which is delivered to a user.

In embodiments in which the first compartment comprises the medicament source and the second compartment comprises the volatile delivery enhancing compound source, medicament vapour is released from the medicament source in the first compartment into the air stream drawn through the aerosol-generating article and volatile delivery enhancing compound vapour is released from the volatile delivery enhancing compound source in the second compartment into the air stream drawn through the aerosol-generating article. The medicament vapour reacts with the volatile delivery enhancing compound vapour in the gas phase to form an aerosol, which is delivered to a user.

Where the first compartment and the second compartment are arranged in series within the aerosol-generating article, the second compartment is preferably downstream of the first compartment so that in use an air stream drawn through the aerosol-generating article passes through the first compartment and then passes through the second compartment. However, it will be appreciated that the second compartment may alternatively be upstream of the first compartment so that in use an air stream drawn through the aerosol-generating article passes through the second compartment and then passes through the first compartment.

In embodiments where the second compartment is downstream of the first compartment, the volatile delivery enhancing compound vapour may react with the medicament vapour in the second compartment. In such embodiments the aerosol-generating article may further comprise a third compartment downstream of the second compartment and the volatile delivery enhancing compound vapour may alternatively or in addition react with the medicament vapour in the third compartment to form an aerosol.

In embodiments where the second compartment is upstream of the first compartment, the volatile delivery enhancing compound vapour may react with the medicament vapour in the first compartment. In such embodiments the aerosol-generating article may further comprise a third compartment downstream of the first compartment and the volatile delivery enhancing compound vapour may alternatively or in addition react with the medicament vapour in the third compartment to form an aerosol.

As used herein, the terms "upstream", "downstream", "proximal" and "distal" are used to describe the relative positions of components, or portions of components, of aerosol-generating articles, aerosol-generating devices and aerosol-generating systems according to the invention.

The aerosol-generating article comprises a proximal end through which in use an aerosol exits the aerosol-generating article. The proximal end may also be referred to as the mouth end. In use, a user draws on the proximal or mouth end of the aerosol-generating article in order to inhale an aerosol generated by the aerosol-generating article. The aerosol-generating article comprises a distal end opposed to the proximal or mouth end. The proximal or mouth end of the aerosol-generating article may also be referred to as the downstream end and the distal end of the aerosol-generating article may also be referred to as the upstream end. Components, or portions of components, of the aerosol-generating article may be described as being upstream or downstream of one another based on their relative positions between the proximal or downstream end and the distal or upstream end of the aerosol-generating article.

The upstream and downstream ends of the aerosol-generating article are defined with respect to the airflow when a user draws on the proximal or mouth end of the aerosol-generating article. Air is drawn into the aerosol-generating article at the distal or upstream end, passes downstream through the aerosol-generating articles and exits the aerosol-generating article at the proximal or downstream end.

As used herein, by "parallel" it is meant that the first compartment and the second compartment are arranged within the aerosol-generating article so that in use a first air stream drawn through the aerosol-generating article passes through the first compartment and a second air stream drawn through the aerosol-generating article passes through the second compartment.

In embodiments in which the first compartment comprises the volatile delivery enhancing compound source and the second compartment comprises the medicament source, volatile delivery enhancing compound vapour is released from the volatile delivery enhancing compound source in the first compartment into the first air stream drawn through the aerosol-generating article and medicament vapour is released from the medicament source in the second compartment into the second air stream drawn through the aerosol-generating article. The volatile delivery enhancing compound vapour in the first air stream reacts with the medicament vapour in the second air stream in the gas phase to form an aerosol, which is delivered to a user.

In such embodiments the aerosol-generating article may further comprise a third compartment downstream of the first compartment and the second compartment and the volatile delivery enhancing compound vapour in the first air stream may mix and react with the medicament vapour in the second air stream in the third compartment to form an aerosol.

In embodiments in which the first compartment comprises the medicament source and the second compartment comprises the volatile delivery enhancing compound source, medicament vapour is released from the medicament source in the first compartment into the first air stream drawn through the aerosol-generating article and volatile delivery enhancing compound vapour is released from the volatile delivery enhancing compound source in the second compartment into the second air stream drawn through the aerosol-generating article. The medicament vapour in the first air stream reacts with the volatile delivery enhancing compound vapour in the second air stream in the gas phase to form an aerosol, which is delivered to a user.

In such embodiments the aerosol-generating article may further comprise a third compartment downstream of the first compartment and the second compartment and the medicament vapour in the first air stream may mix and react with the volatile delivery enhancing compound vapour in the second air stream in the third compartment to form an aerosol.

In particularly preferred embodiments, the aerosol-generating article comprises: a housing comprising: an air inlet; a first compartment in communication with the air inlet, the first compartment comprising a first one of a volatile delivery enhancing compound source and a medicament source; a second compartment in communication with the first compartment, the second compartment comprising a second one of the volatile delivery enhancing compound source and the medicament source; and an air outlet, wherein the air inlet and the air outlet are in communication with each other and configured so that air may pass into the housing through the air inlet, through the housing and out of the housing through the air outlet.

As used herein, the term "air inlet" is used to describe one or more apertures through which air may be drawn into the aerosol-generating article.

As used herein, the term "air outlet" is used to describe one or more apertures through which air may be drawn out of the aerosol-generating article.

In such embodiments, the first compartment and the second compartment are arranged in series from air inlet to air outlet within the housing. That is, the first compartment is downstream of the air inlet, the second compartment is downstream of the first compartment and the air outlet is downstream of the second compartment. In use, a stream of air is drawn into the housing through the air inlet, downstream through the first compartment and the second compartment and out of the housing through the air outlet.

The aerosol-generating article may further comprise a third compartment in communication with: the second compartment; and the air outlet. In use in such embodiments, a stream of air is drawn into the housing through the air inlet, downstream through the first compartment, the second compartment and the third compartment and out of the housing through the air outlet.

The aerosol-generating article may further comprise a mouthpiece in communication with: the second compartment or the third compartment, where present; and the air outlet. In use in such embodiments, a stream of air is drawn into the housing through the air inlet, downstream through the first compartment, the second compartment, the third compartment, where present, and the mouthpiece and out of the housing through the air outlet.

In other preferred embodiments, the aerosol-generating article comprises: a housing comprising: an air inlet; a first compartment in communication with the air inlet, the first compartment comprising a first one of a volatile delivery enhancing compound source and a medicament source; a second compartment in communication with the air inlet, the second compartment comprising a second one of the volatile delivery enhancing compound source and the medicament source; and an air outlet, wherein the air inlet and the air outlet are in communication with each other and configured so that air may pass into the housing through the air inlet, through the housing and out of the housing through the air outlet.

In such embodiments, the first compartment and the second compartment are arranged in parallel from air inlet to air outlet within the housing. The first compartment and the second compartment are both downstream of the air inlet and upstream of the air outlet. In use, a stream of air is drawn into the housing through the air inlet, a first portion of the stream of air is drawn downstream through the first compartment and a second portion of the stream of air is drawn downstream through the second compartment.

The aerosol-generating article may further comprise a third compartment in communication with: one or both of the first compartment and the second compartment; and the air outlet.

The aerosol-generating article may further comprise a mouthpiece in communication with: the first compartment and the second compartment, or the third compartment, where present; and the air outlet.

In further preferred embodiments, the aerosol-generating article comprises: a housing comprising: a first air inlet; a second air inlet; a first compartment in communication with the first air inlet, the first compartment comprising a first one of a volatile delivery enhancing compound source and a medicament source; a second compartment in communication with the second air inlet, the second compartment comprising a second one of the volatile delivery enhancing compound source and the medicament source; and an air outlet, wherein the first air inlet, the second air inlet and the air outlet are in communication with each other and configured so that air may pass into the housing through the first air inlet, through the housing and out of the housing through the air outlet and air may pass into the housing through the second air inlet, through the housing and out of the housing through the air outlet.

In such embodiments, the first compartment and the second compartment are arranged in parallel within the housing. The first compartment is downstream of the first air inlet and upstream of the air outlet and the second compartment is downstream of the second air inlet and upstream of the air outlet. In use, a first stream of air is drawn into the housing through the first air inlet and downstream through the first compartment and a second stream of air is drawn into the housing through the second air inlet and downstream through the second compartment.

The aerosol-generating article may further comprise a third compartment in communication with: one or both of the first compartment and the second compartment; and the air outlet.

The aerosol-generating article may further comprise a mouthpiece in communication with: the first compartment and the second compartment, or the third compartment, where present; and the air outlet.

The housing of the aerosol-generating article may simulate the shape and dimensions of a tobacco smoking article, such as a cigarette, a cigar, a cigarillo or a pipe, or a cigarette pack. In a preferred embodiment, the housing simulates the shape and dimensions of a cigarette.

Where present, the third compartment may comprise one or more aerosol-modifying agents. For example, the third compartment may comprise an adsorbent, such as activated carbon, a flavourant, such as menthol, or a combination thereof.

Where present, the mouthpiece may comprise a filter. The filter may have a low particulate filtration efficiency or very low particulate filtration efficiency. Alternatively, the mouthpiece may comprise a hollow tube.

The first compartment or the second compartment of the aerosol-generating article comprises a volatile delivery enhancing compound source. As used herein, by "volatile" it is meant the delivery enhancing compound has a vapour pressure of at least about 20 Pa. Unless otherwise stated, all vapour pressures referred to herein are vapour pressures at 25° C. measured in accordance with ASTM E1194-07.

In preferred embodiments, the first compartment of the aerosol-generating article comprises a volatile delivery enhancing compound source and the second compartment of the aerosol-generating article comprises a medicament source.

Preferably, the volatile delivery enhancing compound has a vapour pressure of at least about 50 Pa, more preferably at least about 75 Pa, most preferably at least 100 Pa at 25° C.

Preferably, the volatile delivery enhancing compound has a vapour pressure of less than or equal to about 400 Pa, more preferably less than or equal to about 300 Pa, even more preferably less than or equal to about 275 Pa, most preferably less than or equal to about 250 Pa at 25° C.

In certain embodiments, the volatile delivery enhancing compound may have a vapour pressure of between about 20 Pa and about 400 Pa, more preferably between about 20 Pa and about 300 Pa, even more preferably between about 20 Pa and about 275 Pa, most preferably between about 20 Pa and about 250 Pa at 25° C.

In other embodiments, the volatile delivery enhancing compound may have a vapour pressure of between about 50 Pa and about 400 Pa, more preferably between about 50 Pa and about 300 Pa, even more preferably between about 50 Pa and about 275 Pa, most preferably between about 50 Pa and about 250 Pa at 25° C.

In further embodiments, the volatile delivery enhancing compound may have a vapour pressure of between about 75 Pa and about 400 Pa, more preferably between about 75 Pa and about 300 Pa, even more preferably between about 75 Pa and about 275 Pa, most preferably between about 75 Pa and about 250 Pa at 25° C.

In yet further embodiments, the volatile delivery enhancing compound may have a vapour pressure of between about 100 Pa and about 400 Pa, more preferably between about 100 Pa and about 300 Pa, even more preferably between about 100 Pa and about 275 Pa, most preferably between about 100 Pa and about 250 Pa at 25° C.

The volatile delivery enhancing compound may comprise a single compound. Alternatively, the volatile delivery enhancing compound may comprise two or more different compounds.

Where the volatile delivery enhancing compound comprises two or more different compounds, the two or more different compounds in combination have a vapour pressure of at least about 20 Pa at 25° C.

Preferably, the volatile delivery enhancing compound is a volatile liquid.

The volatile delivery enhancing compound may comprise a mixture of two or more different liquid compounds.

The volatile delivery enhancing compound may comprise an aqueous solution of one or more compounds. Alternatively the volatile delivery enhancing compound may comprise a non-aqueous solution of one or more compounds.

The volatile delivery enhancing compound may comprise two or more different volatile compounds. For example, the volatile delivery enhancing compound may comprise a mixture of two or more different volatile liquid compounds.

Alternatively, the volatile delivery enhancing compound may comprise one or more non-volatile compounds and one or more volatile compounds. For example, the volatile delivery enhancing compound may comprise a solution of one or more non-volatile compounds in a volatile solvent or a mixture of one or more non-volatile liquid compounds and one or more volatile liquid compounds.

In one embodiment, the volatile delivery enhancing compound comprises an acid. The volatile delivery enhancing compound may comprise an organic acid or an inorganic acid. Preferably, the volatile delivery enhancing compound comprises an organic acid, more preferably a carboxylic acid, most preferably an alpha-keto or 2-oxo acid.

In a preferred embodiment, the volatile delivery enhancing compound comprises an acid selected from the group consisting of 3-methyl-2-oxopentanoic acid, pyruvic acid, 2-oxopentanoic acid, 4-methyl-2-oxopentanoic acid, 3-methyl-2-oxobutanoic acid, 2-oxooctanoic acid and combinations thereof. In a particularly preferred embodiment, the volatile delivery enhancing compound comprises pyruvic acid.

In a preferred embodiment, the volatile delivery enhancing compound source comprises a sorption element and a volatile delivery enhancing compound sorbed on the sorption element.

As used herein, by "sorbed" it is meant that the volatile delivery enhancing compound is adsorbed on the surface of the sorption element, or absorbed in the sorption element, or both adsorbed on and absorbed in the sorption element. Preferably, the volatile delivery enhancing compound is adsorbed on the sorption element.

The sorption element may be formed from any suitable material or combination of materials. For example, the sorption element may comprise one or more of glass, stainless steel, aluminium, polyethylene (PE), polypropylene, polyethylene terephthalate (PET), polybutylene terephthalate (PBT), polytetrafluoroethylene (PTFE), expanded polytetrafluoroethylene (ePTFE), and BAREX®.

In a preferred embodiment, the sorption element is a porous sorption element.

For example, the sorption element may be a porous sorption element comprising one or more materials selected from the group consisting of porous plastic materials, porous polymer fibres and porous glass fibres.

The sorption element is preferably chemically inert with respect to the volatile delivery enhancing compound.

The sorption element may have any suitable size and shape.

In one preferred embodiment, the sorption element is a substantially cylindrical plug. In one particularly preferred embodiment, the sorption element is a porous substantially cylindrical plug.

In another preferred embodiment, the sorption element is a substantially cylindrical hollow tube. In another particularly preferred embodiment, the sorption element is a porous substantially cylindrical hollow tube.

The size, shape and composition of the sorption element may be chosen to allow a desired amount of volatile delivery enhancing compound to be sorbed on the sorption element.

In a preferred embodiment, between about 20 µl and about 200 µl, more preferably between about 40 µl and about 150 µl, most preferably between about 50 µl and about 100 µl of the volatile delivery enhancing compound is sorbed on the sorption element.

The sorption element advantageously acts as a reservoir for the volatile delivery enhancing compound.

The first compartment or the second compartment of the aerosol-generating article comprises a medicament source.

Preferably, the medicament has a melting point below about 150 degrees Celsius.

Alternatively or in addition, preferably the medicament has a boiling point below about 300 degrees Celsius.

In certain preferred embodiments, the medicament comprises one or more aliphatic or aromatic, saturated or unsaturated nitrogenous bases (nitrogen containing alkaline compounds) in which a nitrogen atom is present in a heterocyclic ring or in an acyclic chain (substitution).

The medicament may comprise one or more compounds selected from the group consisting of: nicotine; 7-Hydroxymitragynine; Arecoline; Atropine; Bupropion; Cathine (D-norpseudoephedrine); Chlorpheneramine; Dibucaine; Dimemorphan, Dimethyltryptamine, Diphenhydramine, Ephedrine, Hordenine, Hyoscyamine, Isoarecoline, Levorphanol, Lobeline, Mesembrine, Mitragynine, Muscatine, Procaine, Pseudo ephedrine, Pyrilamine, Raclopride, Ritodrine, Scopolamine, Sparteine (Lupinidine) and Ticlopidine; tobacco smoke constituents, such as 1,2,3,4 Tetrahydroisoquinolines, Anabasine, Anatabine, Cotinine, Myosmine, Nicotrine, Norcotinine, and Nornicotine; anti-asthmatic drugs, such as Orciprenaline, Propranolol and Terbutaline; anti-angina drugs, such as Nicorandil, Oxprenolol and Verapamil; antiarrhythmic drugs, such as Lidocaine; nicotinic agonists, such as Epibatidine, 5-(2R)-azetidinylmethoxy)-2-chloropyridine (ABT-594), (S)-3-methyl-5-(1-methyl-2-pyrrolidinyl)isoxazole (ABT 418) and (±)-2-(3-Pyridinyl)-I-azabicyclo[2.2.2]octane (RJR-2429); nicotinic antagonists, such as Methyllycacotinine and Mecamylamine; acetyl cholinesterase inhibitors, such as Galantamine, Pyridostigmine, Physostigmine and Tacrine; and MAO-inhibitors, such as Methoxy-N,N-dimethyltryptamine, 5-methoxy-α-methyltryptamine, Alpha-methyltryptamine, Iproclozide, Iproniazide, Isocarboxazide, Linezolid, Meclobemide, N,N-Dimethyltryptamine, Phenelzine, Phenyl ethylamine, Toloxatone, Tranylcypromine and Tryptamine.

The medicament source may comprise a sorption element and a medicament sorbed on the sorption element.

In preferred embodiments, the first compartment of the aerosol-generating article comprises a first one of a volatile delivery enhancing compound source and a nicotine source and the second compartment of the aerosol-generating article comprises a second one of the volatile delivery enhancing compound source and the nicotine source.

In particularly preferred embodiments, the first compartment of the aerosol-generating article comprises a volatile delivery enhancing compound source and the second compartment of the aerosol-generating article comprises a nicotine source. The nicotine source may comprise one or more of nicotine, nicotine base, a nicotine salt, such as nicotine-HCl, nicotine-bitartrate, or nicotine-ditartrate, or a nicotine derivative.

The nicotine source may comprise natural nicotine or synthetic nicotine.

The nicotine source may comprise pure nicotine, a solution of nicotine in an aqueous or non-aqueous solvent or a liquid tobacco extract.

The nicotine source may further comprise an electrolyte forming compound. The electrolyte forming compound may be selected from the group consisting of alkali metal hydroxides, alkali metal oxides, alkali metal salts, alkaline earth metal oxides, alkaline earth metal hydroxides and combinations thereof.

For example, the nicotine source may comprise an electrolyte forming compound selected from the group consisting of potassium hydroxide, sodium hydroxide, lithium oxide, barium oxide, potassium chloride, sodium chloride, sodium carbonate, sodium citrate, ammonium sulfate and combinations thereof.

In certain embodiments, the nicotine source may comprise an aqueous solution of nicotine, nicotine base, a nicotine salt or a nicotine derivative and an electrolyte forming compound.

Alternatively or in addition, the nicotine source may further comprise other components including, but not limited to, natural flavours, artificial flavours and antioxidants.

The volatile nicotine source may comprise a sorption element and nicotine sorbed on the sorption element.

The aerosol-generating article is preferably substantially cylindrical in shape.

The aerosol-generating article may have a transverse cross-section of any suitable shape.

As used herein, the term "longitudinal" is used to describe the direction between the downstream or proximal end and the opposed upstream or distal end of the aerosol-generating article or aerosol-generating device and the term "transverse" is used to describe the direction perpendicular to the longitudinal direction.

Preferably, the aerosol-generating article is of substantially circular transverse cross-section or of substantially elliptical transverse cross-section. More preferably, the aerosol-generating article is of substantially circular transverse cross-section.

The aerosol-generating article may simulate the shape and dimensions of a tobacco smoking article, such as a cigarette, a cigar, a cigarillo or a pipe, or a cigarette pack. In a preferred embodiment, the aerosol-generating article simulates the shape and dimensions of a cigarette.

The aerosol-generating device comprises a cavity configured to receive the first compartment and the second compartment of the aerosol-generating article.

Preferably, the cavity of the aerosol-generating device is substantially cylindrical.

The cavity of the aerosol-generating device may have a transverse cross-section of any suitable shape. For example, the cavity may be of substantially circular, elliptical, triangular, square, rhomboidal, trapezoidal, pentagonal, hexagonal or octagonal transverse cross-section.

As used herein, the term "transverse cross-section" is used to describe the cross-section of the cavity perpendicular to the major axis of the cavity.

Preferably, the cavity of the aerosol-generating device has a transverse cross-section of substantially the same shape as the transverse cross-section of the aerosol-generating article.

In certain embodiments, the cavity of the aerosol-generating device may have a transverse cross-section of substantially the same shape and dimensions as the transverse cross-section of the aerosol-generating article to be received in the cavity in order to maximize conductive thermal transfer from the aerosol-generating device to the aerosol-generating article.

Preferably, the cavity of the aerosol-generating device is of substantially circular transverse cross-section or of substantially elliptical transverse cross-section. Most preferably, the cavity of the aerosol-generating device is of substantially circular transverse cross-section.

Preferably, the length of the cavity of the aerosol-generating device is less than the length of the aerosol-generating article so that when the aerosol-generating article is received in the cavity of the aerosol-generating device the proximal or downstream end of the aerosol-generating article projects from the cavity of the aerosol-generating device.

As used herein, by "length" is meant the maximum longitudinal dimension between the distal or upstream end and the proximal or downstream end of the cavity and aerosol-generating article.

Preferably, the cavity of the aerosol-generating device has a diameter substantially equal to or slightly greater than the diameter of the aerosol-generating article.

As used herein, by "diameter" is meant the maximum transverse dimension of the cavity and aerosol-generating article.

The aerosol-generating device may further comprise a piercing member positioned within the cavity for piercing the first and second compartments of the aerosol-generating article. The piercing member may be formed from any suitable material.

Where the first compartment and the second compartment of the aerosol-generating article are arranged in series within the aerosol-generating article, the piercing member is preferably positioned centrally within the cavity of the aerosol-generating device, along the major axis of the cavity.

Where the first compartment and the second compartment of the aerosol-generating article are arranged in parallel within the aerosol-generating article, the piercing member may comprise a first piercing element positioned within the cavity of the aerosol-generating device for piercing the first compartment of the aerosol-generating article and a second piercing element positioned within the cavity of the aerosol-generating device for piercing the second compartment of the aerosol-generating article.

The aerosol-generating device is configured to heat the first compartment and the second compartment of the aerosol-generating article so that first compartment of the aerosol-generating article has a lower temperature than the second compartment of the aerosol-generating article.

The aerosol-generating device may be configured to substantially simultaneously heat the first compartment and the second compartment of the aerosol-generating article.

Preferably, the aerosol-generating device is configured to heat the first compartment of the aerosol-generating article to a temperature of between about 30 degrees Celsius and about 100 degrees Celsius. In certain embodiments, aerosol-generating device is configured to heat the first compartment of the aerosol-generating article to a temperature of between about 30 degrees Celsius and 70 degrees Celsius.

Preferably, the aerosol-generating device is configured to heat the second compartment of the aerosol-generating article to a temperature of between about 50 degrees Celsius and about 150 degrees Celsius. In certain embodiments, aerosol-generating device is configured to heat the second compartment of the aerosol-generating article to a temperature of between about 50 degrees Celsius and about 100 degrees Celsius.

The aerosol-generating device may further comprise a controller configured to control a supply of power to the external heater.

The aerosol-generating device may further comprise a power supply for supplying power to the external heater and a controller configured to control a supply of power from the power supply to the external heater. Alternatively, the controller of the aerosol-generating device may be configured to control a supply of power from an external power supply to the external heater.

The heater may be an electric heater powered by an electric power supply. Where the heater is an electric heater, the aerosol-generating device may further comprise an electric power supply and a controller comprising electronic circuitry configured to control the supply of electric power from the electric power supply to the electric heater.

The power supply may be a DC voltage source. In preferred embodiments, the power supply is a battery. For example, the power supply may be a Nickel-metal hydride battery, a Nickel cadmium battery, or a Lithium based battery, for example a Lithium-Cobalt, a Lithium-Iron-Phosphate or a Lithium-Polymer battery. The power supply may alternatively be another form of charge storage device such as a capacitor. The power supply may require recharging and may have a capacity that allows for the storage of enough energy for use of the aerosol-generating device with one or more aerosol-generating articles.

Alternatively, the heater may be a non-electric heater, such as a chemical heating means.

The external heater of the aerosol-generating device may comprise one or more external heating elements.

The one or more external heating elements may extend fully or partially along the length of the cavity.

The one or more external heating elements may extend fully or partially around the circumference of the cavity.

The external heater may be configured so that the one or more heating elements are in direct thermal contact with the aerosol-generating article. Alternatively, the external heater may be configured so that the one or more heating elements are positioned close to the aerosol-generating article without contacting it. In other embodiments, the external heater may be configured so that the one or more heating elements are in indirect thermal contact with the aerosol-generating article.

Preferably, the one or more external heating elements are heated electrically. However, other heating schemes may be used to heat the one or more external heating elements. For example, the one or more external heating elements may be heated by conduction from another heat source. Alternatively, each heating element may comprise an infra-red heating element, a photonic source, or an inductive heating element.

Each external heating element may comprise a heat sink, or heat reservoir comprising a material capable of absorbing and storing heat and subsequently releasing the heat over time to the aerosol-forming substrate. The heat sink may be formed of any suitable material, such as a suitable metal or ceramic material. Preferably, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material such as paper. Other suitable materials which release heat via a reversible phase change include paraffin, sodium acetate, naphthalene, wax, polyethylene oxide, a metal, a metal salt, a mixture of eutectic salts or an alloy.

The heat sink or heat reservoir may be arranged such that it is directly in contact with the aerosol-generating article and can transfer the stored heat directly to one or both of the first compartment and the second compartment of the aerosol-generating article. Alternatively, the heat stored in the heat sink or heat reservoir may be transferred to one or both of the first compartment and the second compartment of the aerosol-generating article by means of a thermal conductor, such as a metallic tube.

In a preferred embodiment each external heating element preferably comprises an electrically resistive material. Each heating element may comprise a non-elastic material, for example a ceramic sintered material, such as alumina ($Al_2O_3$) and silicon nitride ($Si_3N_4$), or printed circuit board or silicon rubber. Alternatively, each heating element may comprise an elastic, metallic material, for example an iron alloy or a nickel-chromium alloy. The one or more heating elements may be flexible heating foils on a dielectric substrate, such as polyimide. The flexible heating foils can be shaped to conform to the perimeter of the cavity of the aerosol-generating device. Alternatively, the one or more heating elements may be metallic grid or grids, flexible printed circuit boards, or flexible carbon fibre heaters.

Other suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium- titanium- zirconium-, hafnium-, niobium-, molybdenum-, tantalum-, tungsten-, tin-, gallium- and manganese-alloys, and super-alloys based on nickel, iron, cobalt, stainless steel, Timetal® and iron-manganese-aluminium based alloys. Timetal® is a registered trade mark of Titanium Metals Corporation, 1999 Broadway Suite 4300, Denver, Colo. In composite materials, the electrically resistive material may optionally be embedded in, encapsulated or coated with an insulating material or vice-versa, depending on the kinetics of energy transfer and the external physico-chemical properties required.

The aerosol-generating device may comprise: a first temperature sensor configured to sense the temperature of the first compartment of an aerosol-generating article; and a second temperature sensor configured to sense the temperature of the second compartment of the aerosol-generating article.

In such embodiments, the controller may be configured to control a supply of power to the one or more external heating elements based on the temperature of the first compartment of the aerosol-generating article sensed by the first temperature sensor and the temperature of the second compartment of the aerosol-generating article sensed by the second temperature sensor.

The external heater may comprise one or more external heating elements formed using a metal having a defined relationship between temperature and resistivity. In such embodiments, the metal may be formed as a track between two layers of suitable insulating materials. External heating elements formed in this manner may be used to both heat and monitor the temperature of the first compartment and the second compartment of the aerosol-generating article.

In preferred embodiments, the aerosol-generating device comprises an external heater comprising: a first external heating element configured to heat the first compartment of the aerosol-generating article; and a second external heating element configured to heat the second compartment of the aerosol-generating article; and a controller configured to control a supply of power to the first external heating element and the second external heating element so that the first external heating element has a lower temperature than the second external heating element.

In such embodiments, the first external heating element and the second external heating element are independently controlled by the controller and operate in a different temperature range to control the amount of volatile delivery enhancing compound vapour and nicotine vapour released from the volatile delivery enhancing compound source and the nicotine source respectively.

In such embodiments, the aerosol-generating device may comprise: a first temperature sensor configured to sense the temperature of the first compartment of an aerosol-generating article; and a second temperature sensor configured to sense the temperature of the second compartment of the aerosol-generating article, wherein the controller is configured to control the supply of power to the first external heating element based on the temperature of the first compartment sensed by the first temperature sensor and to control the supply of power to the second external heating element based on the temperature of the second compartment sensed by the second temperature sensor.

The first external heating element may be positioned about a first portion of the perimeter of the cavity and the second external heating element may be positioned about a second portion of the perimeter of the cavity.

Where the first compartment and the second compartment of the aerosol-generating article are arranged in series within the aerosol-generating article with the second compartment downstream of the first compartment, the second external heating element may be positioned downstream of the first external heating element. In such embodiments, the first external heating element may be positioned about a first portion of the perimeter of the cavity and the second external heating element may be positioned about a second portion of the perimeter of the cavity downstream of the first portion of the perimeter of the cavity.

Where the first compartment and the second compartment of the aerosol-generating article are arranged in series within the aerosol-generating article with the second compartment upstream of the first compartment, the second external heating element may be positioned upstream of the first external heating element. In such embodiments, the first external heating element may be positioned about a first portion of the perimeter of the cavity and the second external heating element may be positioned about a second portion of the perimeter of the cavity upstream of the first portion of the perimeter of the cavity.

The first external heating element, the second external heating element or both the first external heating element and the second external heating element may extend fully or partially around the circumference of the cavity Where the first compartment and the second compartment of the aerosol-generating article are arranged in parallel within the aerosol-generating article, the first external heating element may be opposed to the second external heating element. In such embodiments, the first external heating element may be positioned about a first portion of the perimeter of the cavity and the second external heating element may be positioned about a second portion of the perimeter of the cavity opposed to the first portion of the perimeter of the cavity.

The first external heating element, the second external heating element or both the first external heating element and the second external heating element may extend fully or partially along the length of the cavity.

In alternative embodiments, the aerosol-generating device comprises an external heater comprising: a single external heating element having a high density portion configured to heat the second compartment and a low density portion configured to heat the first compartment of the aerosol-generating article so that the first compartment has a lower temperature than the second compartment.

In other embodiments, the aerosol-generating device comprises an external heater comprising: one or more heating elements; a first heat transfer element positioned between the first compartment of the aerosol-generating article and the one or more heating elements; and a second heat transfer element positioned between the second compartment of the aerosol-generating article and the and the one or more heating elements, wherein the first heat transfer element has a lower thermal conductivity than the second heat transfer element.

In such embodiments, the first heat transfer element is positioned between the one or more heating elements and the cavity and the second heat transfer element is positioned between the one or more heating elements and the cavity.

The first heat transfer element and the second heat transfer element may be formed from different materials. The first heat transfer element may be formed from a first material and the second heat transfer element may be formed from a second material, wherein the bulk thermal conductivity of the first material is less than the bulk thermal conductivity of the second material.

The first heat transfer element may be formed from an insulating material. For example, the first heat transfer element may be formed from a material having a bulk thermal conductivity of less than about 5 W per metre Kelvin (W/(m·K)) at 23° C. and a relative humidity of 50% as measured using the modified transient plane source (MTPS) method.

The second heat transfer element may be formed from a conductive material. For example, the second heat transfer element may be formed from a material having a bulk thermal conductivity of greater than about 15 W per metre Kelvin (W/(m·K)) at 23° C. and a relative humidity of 50% as measured using the modified transient plane source (MTPS) method.

Alternatively or in addition, the first heat transfer element and the second heat transfer element may be of different dimensions. For example, the thickness of the first heat transfer element may be greater than the thickness of the second heat transfer element so that the first heat transfer element has a lower thermal conductivity than the second heat transfer element.

In such embodiments, heat transfer from the one or more heating elements to the first compartment of the aerosol-generating article is lower than heat transfer from the one or more heating elements to the second compartment of the aerosol-generating article due to the lower thermal conductivity of the first heat transfer element compared to the second heat transfer element. This results in the first compartment of the aerosol-generating article having a lower temperature than the second compartment of the aerosol-generating article.

In yet further embodiments, the first compartment of the aerosol-generating article has a lower thermal conductivity than the second compartment of the aerosol-generating article.

The first compartment and the second compartment may be formed from different materials. The first compartment may be formed from a first material and the second compartment may be formed from a second material, wherein the bulk thermal conductivity of the first material is less than the bulk thermal conductivity of the second material.

The first compartment may be formed from an insulating material. For example, the first compartment may be formed from a material having a bulk thermal conductivity of less than about 5 W per metre Kelvin (W/(m·K)) at 23° C. and a relative humidity of 50% as measured using the modified transient plane source (MTPS) method.

The second compartment may be formed from a conductive material. For example, the second compartment may be formed from a material having a bulk thermal conductivity of greater than about 15 W per metre Kelvin (W/(m·K)) at 23° C. and a relative humidity of 50% as measured using the modified transient plane source (MTPS) method.

Alternatively or in addition, the first compartment and the second compartment may be of different construction. For example, the thickness of a perimeter of the first compartment may be greater than the thickness of a perimeter of the second compartment so that the first compartment has a lower thermal conductivity than the second compartment.

In such embodiments, heat transfer from the external heater of the aerosol-generating device to the first compartment of the aerosol-generating article is lower than heat transfer from the external heater of the aerosol-generating device to the second compartment of the aerosol-generating article due to the lower thermal conductivity of the first compartment compared to the second compartment. This results in the first compartment of the aerosol-generating article having a lower temperature than the second compartment of the aerosol-generating article.

For the avoidance of doubt, features described above in relation to one embodiment of the invention may also be applicable to other embodiment of the invention. In particular, features described above in relation to aerosol-generating systems according to the invention may also relate, where appropriate to aerosol-generating devices according to the invention, and vice versa.

The invention will now be further described with reference to the accompanying drawings in which.

Figure 1:
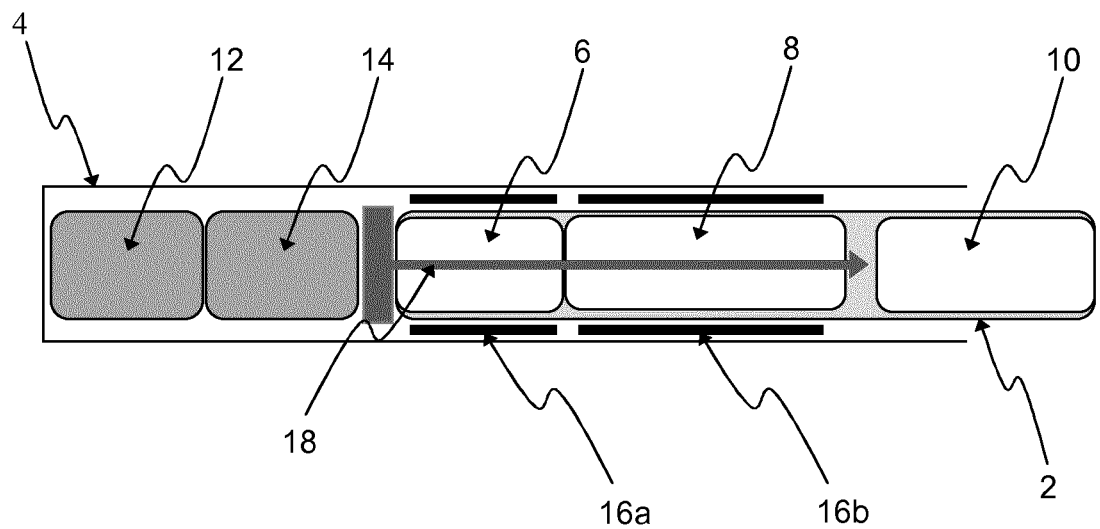
FIG. 1 shows a schematic longitudinal cross-section of an aerosol-generating system according to a first embodiment of the invention.
Figure 3:
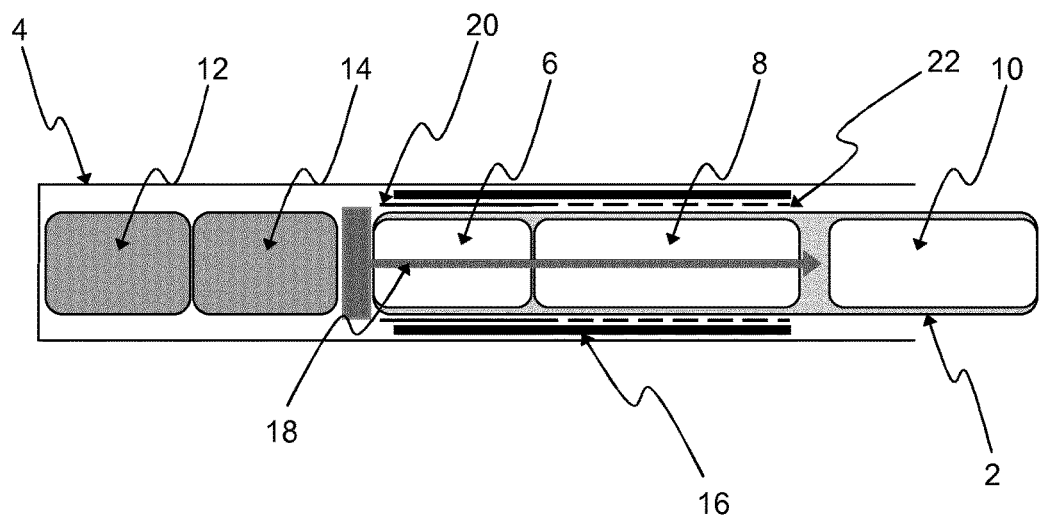
Figure 4:
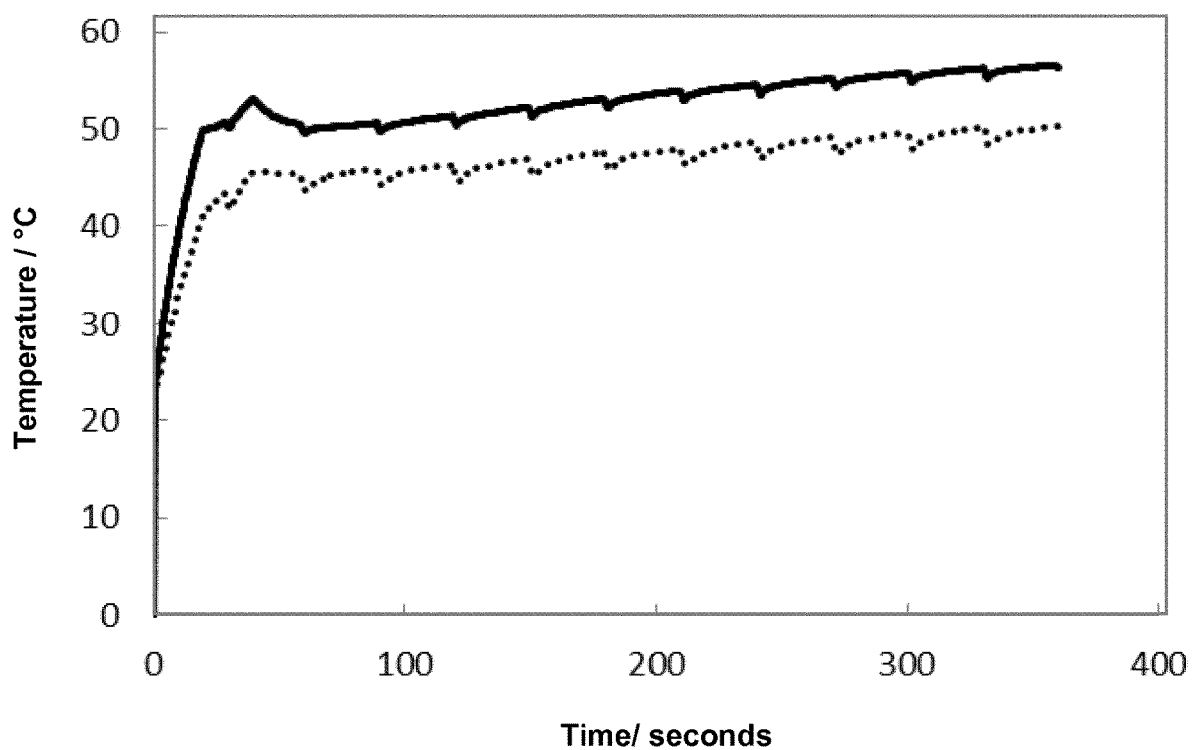

FIG. 3 shows a schematic longitudinal cross-section of an aerosol-generating system according to a third embodiment of the invention; and FIG. 4 shows the temperature of the first compartment and the second compartment of the aerosol-generating article of an aerosol-generating system according to the first embodiment of the invention shown in FIG. 1 as a function of time during operation of the aerosol-generating system according to a Health Canada smoking regime.

FIG. 1 schematically shows an aerosol-generating system according to a first embodiment of the invention comprising an aerosol-generating article 2 and an aerosol-generating device 4.

The aerosol-generating article 2 has an elongate cylindrical shape and comprises a housing comprising a first compartment 6 comprising a volatile delivery enhancing compound source, a second compartment 8 comprising a nicotine source, and a third compartment 10. As shown in FIG. 1, the first compartment 6, the second compartment 8, and the third compartment 10 are arranged in series and in coaxial alignment within the aerosol-generating article 2. The first compartment 6 is located at the distal or upstream end of the aerosol-generating article 2. The second compartment 8 is located immediately downstream of and abuts the first compartment 6. The third compartment 10 is located downstream of the second compartment 8 at the proximal or downstream end of the aerosol-generating article 2. Instead of or in addition to the third compartment 10, the aerosol-generating article 2 may comprise a mouthpiece at the proximal or downstream end thereof.

The upstream and downstream ends of the first compartment 6 and the second compartment 8 of the aerosol-generating article 2 are sealed by frangible barriers (not shown).

The aerosol-generating device 4 comprises a housing comprising a power source 12, a controller 14, an external heater comprising a first external heating element 16a and a second external heating element 16b, a first temperature sensor (not shown) configured to sense the temperature of the first compartment of the aerosol-generating article 2 and a second temperature sensor (not shown) configured to sense the temperature of the second compartment of the aerosol-generating article 2. The first external heating element 16a and the second external heating element 16b are electrically resistive external heating elements.

The aerosol-generating device further comprises an elongate cylindrical cavity in which the aerosol-generating article 2 is received. The length of the cavity is less than the length of the aerosol-generating article 2 so that the proximal or downstream end of the aerosol-generating article 2 protrudes from the cavity.

The power source 12 is a battery. The controller 14 comprises electronic circuitry and is connected to the power supply 12, the first external heating element 16a, the second external heating element 16b, the first temperature sensor and the second temperature sensor. The controller 14 is configured to independently control the supply of power from the power supply 12 to the first external heating element 16a based on the temperature of the first compartment of the aerosol-generating article 2 sensed by the first temperature sensor and to control the supply of power from the power supply 12 to the second external heating element 16b based on the temperature of the second compartment of the aerosol-generating article 2 sensed by the second temperature sensor In the aerosol-generating system according to the first embodiment of the invention the second external heating element 16b of the aerosol-generating device 4 is positioned downstream of the first external heating element 16a thereof.

The first external heating element 16a is positioned about the perimeter of a first portion of the cavity at the distal or upstream end thereof and extends fully around the circumference of the cavity. As shown in FIG. 1, the first external heating element 16a is positioned so that it circumscribes the first compartment 6 of the aerosol-generating article 2.

The second external heating element 16b is positioned about the perimeter of a second portion of the cavity downstream of the first portion of the perimeter of the cavity and extends fully around the circumference of the cavity. As shown in FIG. 1, the second external heating element 16b is positioned so that it circumscribes the second compartment 8 of the aerosol-generating article 2.

The aerosol-generating device 4 further comprises a piercing member 18 positioned centrally within the cavity of the aerosol-generating device 4 and extending along the major axis of the cavity.

In use, as the aerosol-generating article 2 is inserted into the cavity of the aerosol-generating device 4 the piercing member 18 is inserted into the aerosol-generating article 2 and pierces the frangible barriers (not shown) at the upstream and downstream ends of the first compartment 6 and second compartment 8 of the aerosol-generating article 2. This allows a user to draw air into the housing of the aerosol-generating article through the distal or upstream end thereof, downstream through the first compartment 6, the second compartment 8 and the third compartment 10 and out of the housing through the proximal or downstream end thereof.

Volatile delivery enhancing compound vapour is released from the volatile delivery enhancing compound source in the first compartment 6 into the air stream drawn through the aerosol-generating article 2 and nicotine vapour is released from the nicotine source in the second compartment 8 into the air stream drawn through the aerosol-generating article 2. The volatile delivery enhancing compound vapour reacts with the nicotine vapour in the gas phase in the second compartment 8 and the third compartment 10 to form an aerosol, which is delivered to the user through the proximal or downstream end of the aerosol-generating article 2.

In use, the controller 14 balances the concentrations of volatile delivery enhancing compound vapour and nicotine vapour to achieve efficient aerosol formation by independently controlling the supply of power from the power supply 12 to the first external heating element 16a and the second external heating element 16b so that the first compartment 6 of the aerosol-generating article 2 is maintained at a lower temperature than the second compartment 8 thereof.

Figure 2:
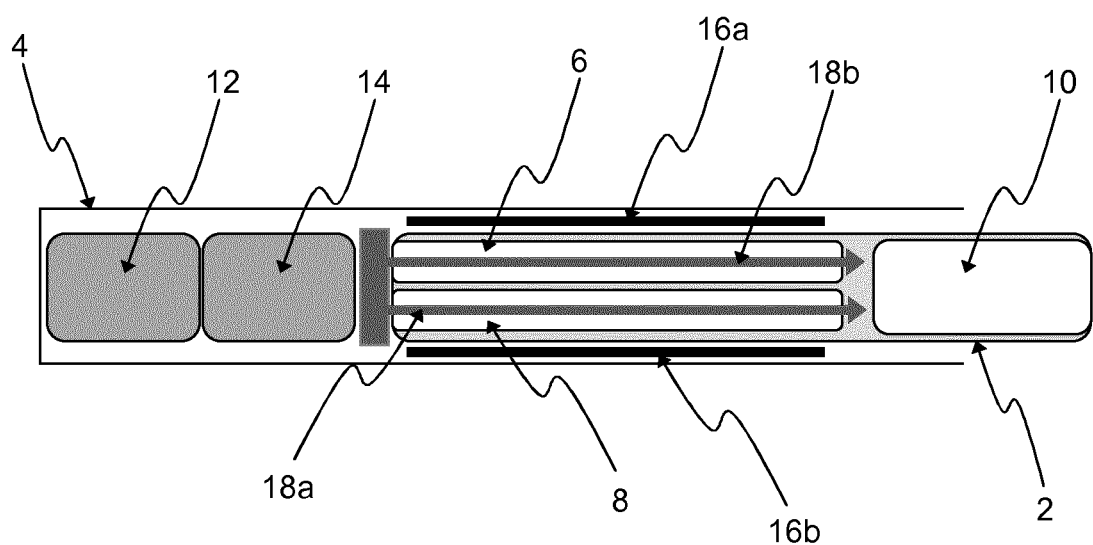
FIG. 2 shows a schematic longitudinal cross-section of an aerosol-generating system according to a second embodiment of the invention.

FIG. 4 is a graph of the temperature of the first compartment 6 (shown by a dashed line) and the second compartment 8 (shown by a solid line) of an aerosol-generating article 2 of an aerosol-generating system according to the first embodiment of the invention shown in FIG. 1 as a function of time during operation of the aerosol-generating system according to a Health Canada smoking regime. The first compartment 6 of the aerosol-generating article 2 comprises a pyruvic acid source. The controller 14 of the aerosol-generating device 4 is configured to control the supply of power from the power supply 12 to the first external heating element 16a so that the first compartment 6 of the aerosol-generating article 2 is maintained at a temperature of between about 40 degrees Celsius and 25 degrees Celsius. The controller 14 of the aerosol-generating device 4 is configured to control the supply of power from the power supply 12 to the second external heating element 16b so that the second compartment 8 of the aerosol-generating article 2 is maintained at a temperature of between about 50 degrees Celsius and 55 degrees Celsius FIG. 2 schematically shows an aerosol-generating system according to a second embodiment of the invention comprising an aerosol-generating article 2 and an aerosol-generating device 4. The aerosol-generating system according to the second embodiment shown in FIG. 2 is of similar construction and operation as the aerosol-generating system according to the first embodiment of the invention shown in FIG. 1.

However, in the aerosol-generating system according to the second embodiment of the invention the first compartment 6 and the second compartment 8 are arranged in parallel within the aerosol-generating article 2. The first compartment 6 is located in an upper first portion of the aerosol-generating article 2 at the distal or upstream end thereof. The second compartment 8 is located in a lower second portion of the aerosol-generating article 2 directly below the upper first portion and abuts the first compartment 6. The third compartment 10 is located downstream of the first compartment 6 and the second compartment 8 at the proximal or downstream end of the aerosol-generating article 2.

In the aerosol-generating system according to the second embodiment of the invention the second external heating element 16b of the aerosol-generating device 4 is opposed to the first external heating element 16a thereof.

The first external heating element 16a is positioned about the perimeter of a first upper portion of the cavity at the distal or upstream end thereof and extends partially around the circumference of the cavity. As shown in FIG. 2, the first external heating element 16a is positioned so that it faces the first compartment 6 of the aerosol-generating article 2.

The second external heating element 16b is positioned about the perimeter of a second lower portion of the cavity opposed to the first portion of the perimeter of the cavity and extends partially around the circumference of the cavity. As shown in FIG. 2, the second external heating element 16b is positioned so that it faces the second compartment 8 of the aerosol-generating article 2.

The piercing member of the aerosol-generating device 4 of the aerosol-generating system according to the second embodiment of the invention comprises a first piercing element 18a and a second piercing element 18b positioned within the cavity of the aerosol-generating device 4 and extending parallel to the major axis of the cavity.

In use, as the aerosol-generating article 2 is inserted into the cavity of the aerosol-generating device 4 the piercing member is inserted into the aerosol-generating article 2 and the first piercing element 18a pierces the frangible barriers (not shown) at the upstream and downstream ends of the first compartment 6 of the aerosol-generating article 2 and the second piercing element 18b pierces the frangible barriers (not shown) at the upstream and downstream ends of the second compartment 8 of the aerosol-generating article 2. This allows a user to draw a first air stream into the housing of the aerosol-generating article through the distal or upstream end thereof and downstream through the first compartment 6 and the third compartment 10 and out of the housing through the proximal or downstream end thereof and to draw a second air stream into the housing of the aerosol-generating article through the distal or upstream end thereof and downstream through the second compartment 8 and the third compartment 10 and out of the housing through the proximal or downstream end thereof.

Volatile delivery enhancing compound vapour is released from the volatile delivery enhancing compound source in the first compartment 6 into the first air stream drawn through the aerosol-generating article 2 and nicotine vapour is released from the nicotine source in the second compartment 8 into the second air stream drawn through the aerosol-generating article 2. The first air stream mixes with the second air stream in the third compartment 10 and the volatile delivery enhancing compound vapour reacts with the nicotine vapour in the gas phase to form an aerosol, which is delivered to the user through the proximal or downstream end of the aerosol-generating article 2.

In use, the controller 14 balances the concentrations of volatile delivery enhancing compound vapour and nicotine vapour to achieve efficient aerosol formation by independently controlling the supply of power from the power supply 12 to the first external heating element 16a and the second external heating element 16b so that the first compartment 6 of the aerosol-generating article 2 is maintained at a lower temperature than the second compartment 8 thereof.

FIG. 3 schematically shows an aerosol-generating system according to a third embodiment of the invention comprising an aerosol-generating article 2 and an aerosol-generating device 4. The construction of the aerosol-generating article 2 of the aerosol-generating system according to the third embodiment shown in FIG. 3 is identical to the construction of the aerosol-generating article 2 of the aerosol-generating system according to the first embodiment of the invention shown in FIG. 1.

The construction of the aerosol-generating device 4 of the aerosol-generating system according to the third embodiment shown in FIG. 3 is similar to the construction of the aerosol-generating device 4 of the aerosol-generating system according to the first embodiment of the invention shown in FIG. 1.

However, in the aerosol-generating system according to the third embodiment of the invention the aerosol-generating device 4 comprises a single electrically resistive external heating element 16 positioned about the perimeter of the cavity that extends fully around the circumference of the cavity. As shown in FIG. 3, the single external heating element 16 is positioned so that it circumscribes the first compartment 6 of the aerosol-generating article 2 received in the cavity of the aerosol-generating device 4.

In the aerosol-generating system according to the third embodiment of the invention the external heater of the aerosol-generating device 4 further comprises a first heat transfer element 20 positioned between the single external heating element 16 and the first compartment 6 of the aerosol-generating article 2 received in the cavity of the aerosol-generating device 4. The external heater also further comprises a second heat transfer element 22 positioned between the single external heating element 16 and the second compartment 8 of the aerosol-generating article 2 received in the cavity of the aerosol-generating device 4. The second heat transfer element 22 is positioned downstream of the first heat transfer element 20 and has a higher thermal conductivity than the first heat transfer element 20.

The first heat transfer element 20 is positioned about the perimeter of a first portion of the cavity at the distal or upstream end thereof and extends fully around the circumference of the cavity. As shown in FIG. 3, the first heat transfer element 20 is positioned so that it circumscribes the first compartment 6 of the aerosol-generating article 2 received in the cavity of the aerosol-generating device 4.

The second heat transfer element 22 is positioned about the perimeter of a second portion of the cavity downstream of the first portion of the perimeter of the cavity and extends fully around the circumference of the cavity. As shown in FIG. 3, the second heat transfer element 22 is positioned so that it circumscribes the second compartment 8 of the aerosol-generating article 2 received in the cavity of the aerosol-generating device 4.

The aerosol-generating device 4 further comprises a piercing member 18 positioned centrally within the cavity of the aerosol-generating device 4 and extending along the major axis of the cavity.

In use, as the aerosol-generating article 2 is inserted into the cavity of the aerosol-generating device 4 the piercing member 18 is inserted into the aerosol-generating article 2 and pierces the frangible barriers (not shown) at the upstream and downstream ends of the first compartment 6 and second compartment 8 of the aerosol-generating article 2. This allows a user to draw air into the housing of the aerosol-generating article through the distal or upstream end thereof, downstream through the first compartment 6, the second compartment 8 and the third compartment 10 and out of the housing through the proximal or downstream end thereof.

Volatile delivery enhancing compound vapour is released from the volatile delivery enhancing compound source in the first compartment 6 into the air stream drawn through the aerosol-generating article 2 and nicotine vapour is released from the nicotine source in the second compartment 8 into the air stream drawn through the aerosol-generating article 2. The volatile delivery enhancing compound vapour reacts with the nicotine vapour in the gas phase in the second compartment 8 and the third compartment 10 to form an aerosol, which is delivered to the user through the proximal or downstream end of the aerosol-generating article 2.

In use, the controller 14 controls the supply of power from the power supply 12 to the single external heating element 16. To balance the concentrations of volatile delivery enhancing compound vapour and nicotine vapour to achieve efficient aerosol formation, the first heat transfer element 20 and the second heat transfer element 22 of the external heater are configured so that the first compartment 6 of the aerosol-generating article 2 is maintained at a lower temperature than the second compartment 8 thereof.

The invention has been exemplified above by reference to aerosol-generating systems comprising aerosol-generating devices comprising external heaters comprising one or more electrically resistive external heating elements. However, it will be appreciated that aerosol-generating systems and aerosol-generating devices according to the invention may comprise other types of external heaters.

The invention claimed is:

1. An aerosol-generating system, comprising:
an aerosol-generating article, comprising:
a first compartment comprising a first one of a volatile delivery enhancing compound source and a medicament source; and
a second compartment comprising a second one of the volatile delivery enhancing compound source and the medicament source; and
an aerosol-generating device, comprising:
a cavity configured to receive the first compartment and the second compartment of the aerosol-generating article; and
an external heater positioned about a perimeter of the cavity, the external heater comprising a single external heating element such that, when the first compartment and the second compartment are received in the cavity, the first compartment and the second compartment are at least partially surrounded by the single external heating element,
wherein the external heater further comprises a first heat transfer element positioned between the single external heating element and the first compartment and a second heat transfer element positioned between the single external heating element and the second compartment, when the first compartment and the second compartment are received in the cavity,
wherein the aerosol-generating device is configured to heat the first compartment and the second compartment of the aerosol-generating article so that the first compartment of the aerosol-generating article has a lower temperature than the second compartment of the aerosol-generating article, and
wherein a thickness of the first heat transfer element is greater than a thickness of the second heat transfer element so that the first heat transfer element has a lower thermal conductivity than the second heat transfer element.

2. The aerosol-generating system according to claim 1, wherein the aerosol-generating device is configured to heat the first compartment of the aerosol-generating article to a temperature between 40 degrees Celsius and 45 degrees Celsius.

3. The aerosol-generating system according to claim 2, wherein the aerosol-generating device is configured to heat the second compartment of the aerosol-generating article to a temperature of between 50 degrees Celsius and 55 degrees Celsius.

4. The aerosol-generating system according to claim 1, wherein the volatile delivery enhancing compound comprises an acid.

5. The aerosol-generating system according to claim 4, wherein the acid is selected from the group consisting of 3-methyl-2-oxovaleric acid, pyruvic acid, 2-oxovaleric acid, 4-methyl-2-oxovaleric acid, 3-methyl-2-oxobutanoic acid, 2-oxooctanoic acid, and combinations thereof.

6. The aerosol-generating system according to claim 5, wherein the acid is pyruvic acid.

7. The aerosol-generating system according claim 1, wherein the aerosol-generating device further comprises:
 a controller configured to control a supply of power to the first external heating element and the second external heating element so that the first external heating element has a lower temperature than the second external heating element.

8. The aerosol-generating system according to claim 7, wherein the aerosol-generating device further comprises:
 a first temperature sensor configured to sense a temperature of the first compartment of the aerosol-generating article; and
 a second temperature sensor configured to sense a temperature of the second compartment of the aerosol-generating article,
 wherein the controller is further configured to control the supply of power to the single external heating element based on the temperature of the first compartment of the aerosol-generating article sensed by the first temperature sensor and to control the supply of power to the single external heating element based on the temperature of the second compartment of the aerosol-generating article sensed by the second temperature sensor.

9. The aerosol-generating system according to claim 1, wherein the first heat transfer element is positioned about a first portion of the perimeter of the cavity and the second heat transfer element is positioned about a second portion of the perimeter of the cavity downstream of the first portion of the perimeter of the cavity.

10. The aerosol-generating system according to claim 1, wherein one or both of the first compartment and the second compartment of the aerosol-generating article are sealed by one or more frangible seals.

11. The aerosol-generating system according to claim 1, wherein the aerosol-generating device further comprises:
 a piercing member positioned within the cavity and configured to pierce the first compartment and the second compartment of the aerosol-generating article.

12. An aerosol-generating system, comprising:
 an aerosol-generating article, comprising:
  a first compartment comprising a first one of a volatile delivery enhancing compound source and a medicament source; and
  a second compartment comprising a second one of the volatile delivery enhancing compound source and the medicament source; and
 an aerosol-generating device, comprising:
  a cavity configured to receive the first compartment and the second compartment of the aerosol-generating article; and
  an external heater comprising a first external heating element and a second external heating element,
 wherein the first compartment and the second compartment are arranged in parallel within the aerosol-generating article, the first compartment being disposed in an upper first portion of the cavity and the second compartment being disposed in a lower second portion of the cavity abutting the first compartment, such that the first external heating element is positioned solely about a perimeter of the first upper portion of the cavity, facing the first compartment, and the second external heating element is positioned solely about a perimeter of the second lower portion of the cavity opposite the first upper portion of the cavity, facing the second compartment, and
 wherein the aerosol-generating device is configured to heat the first compartment and the second compartment so that the first compartment has a lower temperature than the second compartment.

13. The aerosol-generating system according to claim 12, wherein the aerosol-generating device is further configured to heat the first compartment to a temperature between 40 degrees Celsius and 45 degrees Celsius.

14. The aerosol-generating system according to claim 13, wherein the aerosol-generating device is further configured to heat the second compartment to a temperature of between 50 degrees Celsius and 55 degrees Celsius.

15. The aerosol-generating system according to claim 12, wherein the volatile delivery enhancing compound comprises an acid selected from the group consisting of 3-methyl-2-oxovaleric acid, pyruvic acid, 2-oxovaleric acid, 4-methyl-2-oxovaleric acid, 3-methyl-2-oxobutanoic acid, 2-oxooctanoic acid, and combinations thereof.

16. The aerosol-generating system according claim 12, wherein the aerosol-generating device further comprises:
 a controller configured to control a supply of power to the first external heating element and the second external heating element so that the first external heating element has a lower temperature than the second external heating element.

17. The aerosol-generating system according to claim 12, wherein one or both of the first compartment and the second compartment of the aerosol-generating article are sealed by one or more frangible seals.

18. The aerosol-generating system according to claim 12, wherein the aerosol-generating device further comprises:
 a piercing member positioned within the cavity and configured to pierce the first compartment and the second compartment of the aerosol-generating article.

19. The aerosol-generating system according to claim 16, wherein the aerosol-generating device comprises:
 a first temperature sensor configured to sense a temperature of the first compartment of the aerosol-generating article; and
 a second temperature sensor configured to sense a temperature of the second compartment of the aerosol-generating article,
 wherein the controller is further configured to control the supply of power to the first external heating element based on the temperature of the first compartment of the aerosol-generating article sensed by the first temperature sensor and to control the supply of power to the second external heating element based on the temperature of the second compartment of the aerosol-generating article sensed by the second temperature sensor.

* * * * *